(12) United States Patent
Koike et al.

(10) Patent No.: US 8,389,429 B2
(45) Date of Patent: Mar. 5, 2013

(54) COMPOSITE CERAMIC BODY

(75) Inventors: Kazuhiko Koike, Okazaki (JP);
Masayuki Kobayashi, Kuwana (JP)

(73) Assignees: Nippon Soken, Inc., Nishio (JP); Denso Corporation, Kariya (JP)

( * ) Notice: Subject to any disclaimer, the term of this patent is extended or adjusted under 35 U.S.C. 154(b) by 430 days.

(21) Appl. No.: 12/487,111

(22) Filed: Jun. 18, 2009

(65) Prior Publication Data

US 2009/0318281 A1 Dec. 24, 2009

(30) Foreign Application Priority Data

Jun. 19, 2008 (JP) .................................. 2008-160284
Jun. 5, 2009 (JP) .................................. 2009-136054

(51) Int. Cl.
*C04B 35/488* (2006.01)
(52) U.S. Cl. ........................................ 501/105; 204/424
(58) Field of Classification Search .................. 501/103, 501/105, 153; 423/608, 625, 628; 204/424–429
See application file for complete search history.

(56) References Cited

U.S. PATENT DOCUMENTS

| | | | |
|---|---|---|---|
| 4,657,877 A * | 4/1987 | Becher et al. .................. | 501/89 |
| 5,728,636 A | 3/1998 | Nawa et al. | |
| 5,863,850 A | 1/1999 | Nawa et al. | |
| 6,298,726 B1 | 10/2001 | Adachi et al. | |
| 7,148,167 B2 * | 12/2006 | Shikata et al. ................ | 501/105 |
| 2009/0000352 A1 | 1/2009 | Koike et al. | |

FOREIGN PATENT DOCUMENTS

| | | |
|---|---|---|
| JP | 08-015213 | 1/1996 |
| JP | 2703207 | 10/1997 |
| JP | 11-071166 | 3/1999 |
| JP | 2000-005180 | 1/2000 |
| JP | 2009-008435 | 1/2009 |

OTHER PUBLICATIONS

Author Unknown, "Microstructure Control of Dispersion-Strengthened Ceramics"; Ceramic Advanced Materials—Strength and Microstructure, Apr. 1991, pp. 275-279 (with partial English translation).
Japanese Office Action dated Jun. 29, 2010, issued in corresponding Japanese Application No. 2009-136054, with English translation.

* cited by examiner

*Primary Examiner* — Karl Group
(74) *Attorney, Agent, or Firm* — Nixon & Vanderhye P.C.

(57) ABSTRACT

A composite ceramic body with increased strength is disclosed. The composite ceramic body, composed of a matrix of alumina particles with a mean particle diameter ranging from 0.7 to 1.8 μm and nano-zirconia particles with a particle diameter of 0.15 μm or less, wherein the alumina particles and the nano-zirconia particles fall in a respective weight percentage ratio ranging from 80:20 to 95:5 with a relative density of 93% or more and wherein in a cross section, a total sum of surface areas of pores, having cross-sectional areas equal to or greater than surface areas of circles having the same diameters as a mean particle diameter of the alumina particles, falls in a value of 2.2% or less based on a whole of the cross-sectional areas.

8 Claims, 5 Drawing Sheets

COMPOSITE CERAMIC BODY

CROSS-REFERENCE TO RELATED APPLICATION

This application is based on and claims the benefit of priority from earlier Japanese Patent Application Nos. 2008-160284 filed on Jun. 19, 2008 and 2009-136054 filed on Jun. 5, 2009, the descriptions of which are incorporated herein by references.

BACKGROUND OF THE INVENTION

1. Technical Field of the Invention

The present invention relates to a composite ceramic body, composed of a matrix of alumina particles to which nano-zirconia particles are dispersed, which is used for a gas sensor.

2. Related Art

An engine of a motor vehicle has an exhaust system on which a gas sensor is mounted for measuring an oxygen concentration or the like of exhaust gases. The gas sensor incorporates therein a gas sensing element composed of ceramic.

The gas sensing element has a structure with an external surface adapted to be brought into contact with exhaust gases. During startup of the engine, exhaust gases are emitted containing water droplets spattering across the gas sensing element.

Meanwhile, in order to activate the gas sensing element, the gas sensing element is heated to temperatures of, for instance, 600° C. or more in use.

If the water droplets adhere to a surface of the gas sensing element, these areas tend to be rapidly cooled, thereby suffering thermal shock. This results in a risk of cracks or chips occurring to the gas sensing element.

To avoid such thermal shock, there has been known a control of minimizing a temperature increase in the gas sensing element during the startup of the engine with increased likelihood of bearing sputtering water droplets as disclosed in Japanese Patent Application Publication No. 8-15213.

Further, there has been known a ceramic material, having increased strength and fracture toughness, which is composed of nano-composite material in which nano particles are dispersed in a matrix as disclosed in Japanese Patent No. 2703207.

However, minimizing the temperature increase of the gas sensing element during the startup of the engine results in a delay in activating the gas sensing element during the startup of the engine. Thus, there is a risk of degradation occurring to the detecting precision of exhaust gases during the startup of the engine.

Furthermore, since exhaust gases tend to contain harmful gas compounds during the startup of the engine, it is quite important to detect the oxygen concentration in exhaust gases during the startup of the engine for controlling an air/fuel ratio. In addition, minimizing the temperature increase of the gas sensing element during the startup of the engine results in a delay in activating the gas sensing element and such an expedient is unfavorable.

Although the temperature of the gas sensing element is desired to immediately rise up to an activating temperature from the beginning of the startup of the engine, there is a need to consider the risk of cracks (water-incursion cracks) occurring to the gas sensing element due to attached water droplets as set forth above.

In order to avoid the occurrence of water-incursion cracks, a ceramic material, forming the surface of the gas sensing element, needs to have strength withstanding thermal shock.

For the ceramic material having increased strength, it has been known to use nano-composite material as described above.

However, even if a composite ceramic body is made of materials using the nano-composite material, it has been difficult to obtain adequate strength.

With the nano-composite material, nano particles are hard to disperse with an increased risk of causing the nano particles to agglutinate, resulting in an increased likelihood of causing the formation of pores in the composite ceramic body.

As a result of dedicated studies conducted by the instant inventors, it has been found that sizes of the pores have correlations with particle diameters of the particles forming the matrix and the sizes and a volume of the pores in the composite ceramic body have an affect on strength.

SUMMARY OF THE INVENTION

The present invention has been completed with a view to addressing the above issues of the related art and has an object to provide a composite ceramic body having increased strength.

The present invention is directed to a composite ceramic body comprising a matrix of alumina particles having a mean particle diameter ranging from 0.7 to 1.8 µm and nano-zirconia particles, having particle diameters of 0.15 µm or less, which are dispersed in the matrix, wherein a content of the alumina particles and the nano-zirconia particles falls in a weight percentage ratio ranging from 80:20 to 95:5 respectively with a relative density of 93% or more. The total sum of surface areas of pores, having cross-sectional areas equal to or greater than those of the alumina particles with a mean particle diameter among pores present on an arbitrarily cutout cross section, has a share in a whole of the cross section at a pore surface area percentage of 2.2% or less.

The composite ceramic body of the present invention is a composite ceramic body containing the nano-zirconia particles dispersed in the matrix of the alumina particles for improving strength of alumina.

Further, a pore, having a large cross-sectional area in the composite ceramic body, becomes a starting point of inducing fractures when applied with stress, resulting in a reduction in strength of the composite ceramic body.

The instant inventors have found out a result described below. That is, it is likely that the composite ceramic body has pores (i.e., pores each having a surface area equal to or greater than that of an average alumina particle) each having a cross-sectional area equal to or greater than that of a circle with a diameter equal to or greater than a mean particle diameter of the alumina particles contained in the composite ceramic body. With such a structure, if a total surface area of the pores, present on a cross section, has a percentage (pore surface area percentage) shared in a whole of the cross section, exceeds a certain range, then, it becomes difficult to obtain sufficient strength.

With the composite ceramic body, as shown in FIG. 7, a large number of alumina particles 2 are stacked on one another with the resultant formation of a pore 40 in the form of a clearance present between grain boundary layers. The pore 40 usually has an equivalent circle diameter smaller than particle diameters of surrounding alumina particles 2. The pore 40, smaller than a mean particle diameter of the alumina particles, is a clearance formed as a result of the alumina particles 2 being densely stacked on each other. Thus, there is no risk of stress concentrating at the pore 40 to cause a drop in strength.

As shown in FIG. 8, however, the pore 40 (specified pore 4), having the same cross sectional area as that of a circle with a diameter equal to or greater than a mean particle diameter of the alumina particles 2, is likely to be present because of a deficit of the alumina particles 2. In such a case, the alumina particles 2, present around such a specified pore 4, have no areas to be backed up in areas near the specified pore 4. Under such a situation, if stress occurs on the alumina particles 2, then, stress concentrates on the area around the specified pore 4. As a result of such occurrence, it is considered that cracks occur from a starting point of the specified pore 4, causing degradation in strength.

If the number of such specified pores 4 is adequately small, no issue arises in the degradation of strength of the composite ceramic body. In addition, it has been found out that if the pore surface area percentage of the specified pores 4 increases, degradation occurs in strength of the composite ceramic body.

The composite ceramic body of the present invention contemplates to have a pore surface area percentage limited to a value of 2.2% or less representing a range that can ensure adequate strength.

Thus, the present invention makes it possible to provide a composite ceramic body having increased strength.

Figure 7:
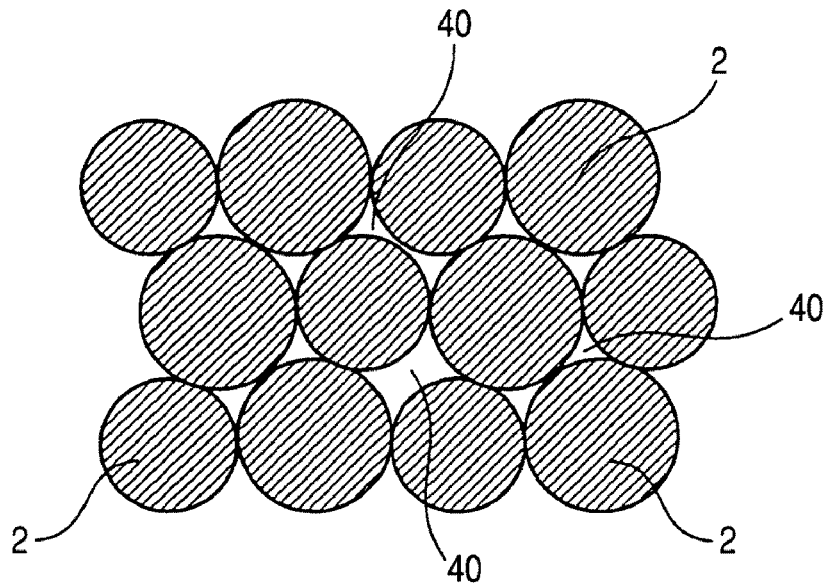
FIG. 7 is a typical view of the structure of alumina particles of a composite ceramic body in which only pores, having equivalent circle diameters smaller than a mean particle diameter of the alumina particles, are present.
Figure 8:
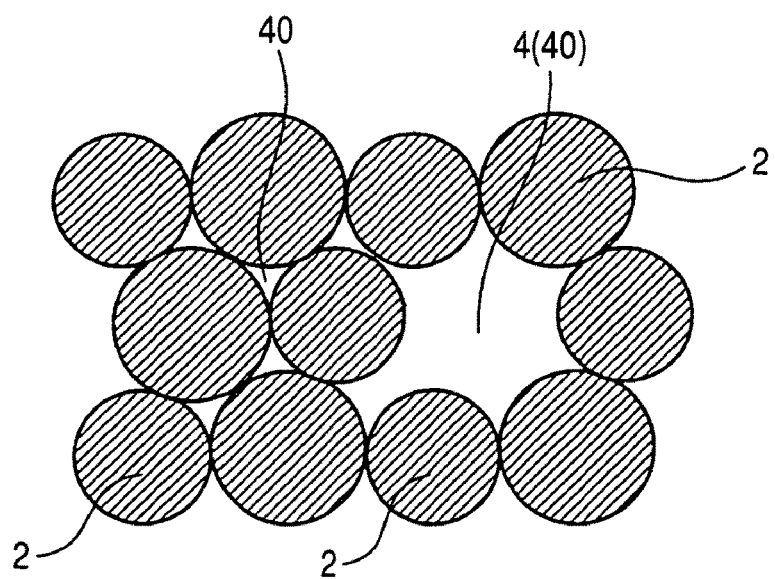
FIG. 8 is a typical view of an array condition of alumina particles of a composite ceramic body in which specified pores are present.

Further, FIGS. 7 and 8 typically represent the structures of the alumina particles in the composite ceramic bodies.

DETAILED DESCRIPTION OF PREFERRED EMBODIMENTS

A composite ceramic body according to the present invention is directed to the composite ceramic body having the alumina particles with the matrix in which the nano zirconia particles are dispersed as set forth above.

The alumina particle and the nano-zirconia particles are present in a weight percentage ranging from 95:5 to 80:20 respectively. This allows the alumina particles to have reinforced boundary layers with suppressed growth of the alumina particles, thereby enabling the composite ceramic structure to ensure strength. If a nano-zirconia content increases beyond the above-described weight percentage, it is likely that the nano-zirconia will coagulate. Thus, zirconia particles with large particle diameters are caused to exist as defects in the matrix of the alumina particles, thereby causing a risk of a drop occurring to strength of the composite ceramic body. In contrast, if the nano-zirconia content decreases below the above-described weight percentage, degradations occur in strength of the boundary layers of the alumina particles, while making it difficult to suppress the growth of the alumina particles. This results in a risk of a drop occurring to strength of the composite ceramic body.

If the composite ceramic body has a relative density (described below) less than 93%, there is a risk of a difficulty occurring to the ceramic composite body in adequately improving strength.

If the alumina particles have a mean particle diameter less than 0.7 µm, a drop occurs in the required firing temperatures with a resultant difficulty sustaining a high relative density. This causes a risk of a reduction in strength of the composite ceramic body. On the contrary, if the mean particle diameter exceeds 1.8 µm, the growth of the alumina particles is inadequately suppressed, causing a risk of a drop in strength of the composite ceramic body.

If the particle diameters of the nano-zirconia particles exceed 0.15 µm, stress occurs in an area in which such nano-zirconia particles are present, resulting in a risk of a starting point of cracks or the like occurring to the composite ceramic body.

The composite ceramic body has a cross section in the presence of pores with a pore surface area percentage equal to or less than 2.2%. The pore surface area percentage represents a percentage of a total surface area of the specified pores occupied in a whole of the cross section of the composite ceramic body. The specified pores have a cross sectional area equivalent to a circle with a diameter equal to or greater than the mean particle diameter of the alumina particles.

If the pore surface area percentage exceeds 2.2%, then, it is likely that when applied with stress, the nano-zirconia particles easily become a starting point of cracks with a resultant difficulty of having adequate strength.

The pore surface area percentage can be regulated upon altering conditions such as a kind of and the amount of additives like dispersant and binder, etc., and degreasing or the like when preparing the composite ceramic body.

The composite ceramic body may be preferably used to form a part of a gas sensor for detecting a concentration of measuring gases.

The composite ceramic body has high strength. Therefore, when applying the composite ceramic body as a ceramic material to form a surface of a gas sensing element, the gas sensing element can withstands thermal shock, thereby enabling the prevention of water-incursion cracks mentioned above.

The alumina particles and nano-zirconia particles may preferably be present in a content ranging from 92.5:7.5 to 85:15 in terms of a weight percentage ratio of both particles.

In such a case, it becomes possible to reinforce the grain boundaries of the alumina particles with the suppression in growth of the alumina particles, thereby enabling a composite ceramic body to have increased strength.

Further, the above-described pore surface area percentage may preferably fall in a range equal to or less than 1.5%.

In such a case, it becomes possible to obtain a composite ceramic body with further increased strength.

(First Embodiment)

A composite ceramic body of a first embodiment according to the present invention will be described below.

Figure 2:
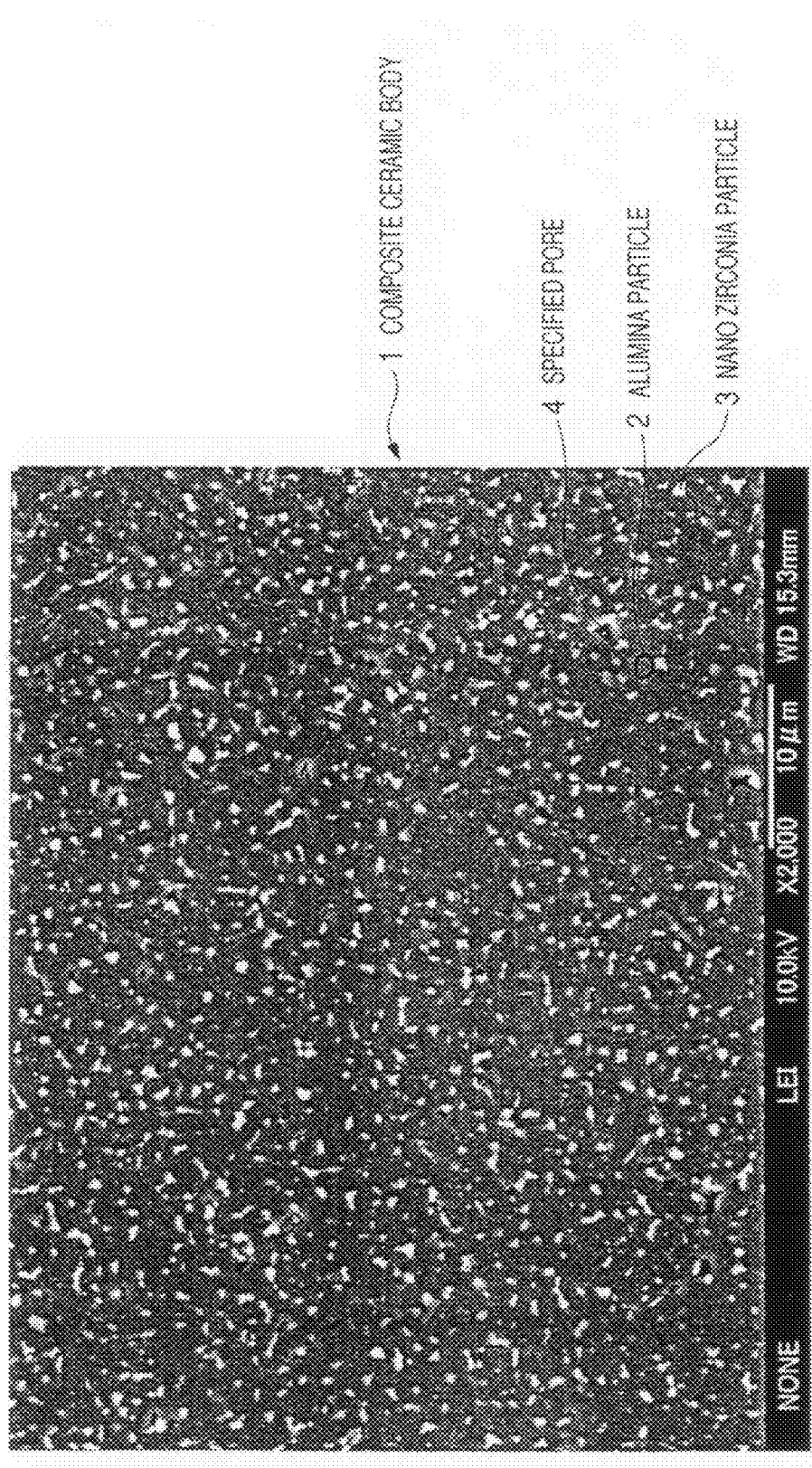
FIG. 2 is a drawing substitute photograph showing a SEM observation in the first embodiment.

As shown in FIG. 2, the composite ceramic body 1 of the present embodiment is made of alumina particles 2 with a matrix in which nano-zirconia particles 3 are dispersed.

The alumina particles 2 have a mean particle diameter ranging from 0.7 to 1.8 μm and the nano-zirconia particles 3 have a mean particle diameter equal to or less than 0.15 μm. Moreover, the alumina particles 2 and the nano-zirconia particles 3 are blended with a weight percentage ratio ranging from 80:20 to 95:5. In addition, the composite ceramic body 1 has a relative density of 93% or more.

The composite ceramic body has a cross section, cut in an arbitrary profile, which has a pore surface area percentage of 2.2% or less that represents a percentage of a total surface area of specified pores 4, having a cross-sectional area equivalent to a circle with its diameter equal to or greater than a mean particle diameter of the alumina particles, which is shared in a whole of the cross section.

First, a method of manufacturing the composite ceramic body will be described below.

Alumina particles with a mean particle diameter of 0.3 μm and nano-zirconia particles with a mean particle diameter of 20 nm were blended in a given weight percentage shown in Table 1. A binder, a plasticizer, a dispersant and an antifoam agent were mixed to an organic solvent mainly composed of ethanol in a ball mill. Thereafter, the resulting mixture was filtered to remove foreign substances, after which defoaming and density adjustment are conducted to obtain slurry.

Subsequently, sheet forming was conducted by a doctor blade method using the resulting slurry, thereby obtaining plural sheets. The resulting sheets are dried, stacked and pressure bonded to each other, after which the sheets were cut into plural pieces in a given dimension.

The resulting plural pieces were subjected to degreasing treatment at a maximum temperature of 500° C. for 25 hours, thereby preparing firing samples. The firing samples were placed in an electrical furnace (under atmospheric pressure) to be fired under a firing pattern in which the firing samples were raised in temperature at a setting time rate of 150° C./hour and kept therein at the setting temperature for one hour, after which the firing samples were cooled by furnace cooling to room temperature.

With such a manufacturing method conducted in a manner described above, test pieces (test pieces E1 to E29) of the composite ceramic bodies were obtained for carrying out properties tests.

Table 1 shows firing set temperatures (firing temperatures) of the test pieces E1 to E29 and test pieces C1 to C6.

Further, as comparative examples, test pieces (Test pieces Nos. C1 to C6) of the composite ceramic bodies were prepared in which at least one item of a mean particle diameter of the alumina particles, a mean particle diameter of the nano-zirconia particles, a weight percentage ratio between the alumina particles and the nano-zirconia particles, a relative density and a bending strength of the composite ceramic body was deviated from the condition mentioned above.

Furthermore, the pore surface area percentages were adjusted upon altering the kinds of dispersants, binders or the like, degreasing conditions and firing conditions, etc.

That is, the pore surface area percentage could be adjusted in combination of the following three conditions:

(1) Coagulating Condition between Alumina Particles and Nano-zirconia Particles:

Causing the particles to coagulate results in an increase in pore diameter with an increase in the number of pores. With the particles better dispersed, the pores become small in size with a decrease in the number of pores. The coagulation of the particles can be adjusted upon varying the kind of and the amount of dispersants being added.

(2) Degreasing Condition:

Conducting the degreasing for a short time interval results in an increase in pore diameter. Conducting the degreasing for a long time period of time results in a decrease in size of the pores. The degreasing condition can be adjusted upon varying a kind of and the amount of the binder, etc., being added.

(3) Firing Condition:

The lower the firing temperature, the larger will be the number of pores being formed. In contrast, the higher the firing temperature, the smaller will be the number of pores being formed. The firing condition can be adjusted upon selecting materials to be used.

By appropriately altering the combination of the three conditions set forth above, the pore surface area percentages of the test pieces Nos. E1 to E29 and the test pieces Nos. C1 to C6 were adjusted.

In manufacturing the composite ceramic bodies (test pieces Nos. E1 to E29) of the present invention, the degreasing times of the degreasing condition were extended to be 1.9 times or more of the time allocated to the comparative examples (test pieces Nos. C1 to C6), thereby achieving a decrease in the pore surface area percentages.

Tests were conducted on the composite ceramic bodies (test pieces Nos. E1 to E29) of the present invention and the composite ceramic bodies (test pieces Nos. C1 to C6), prepared in such a way mentioned above, to check weight percentages of alumina: zirconia and the firing temperatures in terms of the pore surface area percentages, bending strengths, the mean particle diameters of alumina particles, the mean particle diameters of nano-zirconia particles and relative densities, all of which are indicated on Table 1.

TABLE 1

|  | Alumina:Zirconia (In Weight Ratio) | Firing Temper. (° C.) | Pore Surface Area Percent. (%) | Bend. Strength (MPa) | Mean Parti. Diam. of Alumina (μm) | Mean Parti. Diam. of Zirconia (μm) | Relative Density (%) |
| --- | --- | --- | --- | --- | --- | --- | --- |
| Compara. Exam. 1 | 99:1 | 1450 | 1.80 | 520 | 1.2 | 0.10 | 97 |
| Embod. 1 | 95:5 | 1600 | 0.81 | 771 | 1.8 | 0.12 | 98 |
| Embod. 2 | 95:5 | 1550 | 1.24 | 756 | 1.5 | 0.12 | 98 |
| Embod. 3 | 95:5 | 1500 | 1.61 | 765 | 1.2 | 0.11 | 97 |
| Embod. 4 | 95:5 | 1450 | 1.75 | 681 | 1.0 | 0.11 | 96 |
| Embod. 5 | 92.5:7.5 | 1600 | 0.63 | 990 | 1.1 | 0.12 | 98 |
| Embod. 6 | 92.5:7.5 | 1550 | 1.19 | 898 | 1.0 | 0.11 | 96 |

TABLE 1-continued

| | Alumina:Zirconia (In Weight Ratio) | Firing Temper. (° C.) | Pore Surface Area Percent. (%) | Bend. Strength (MPa) | Mean Parti. Diam. of Alumina (μm) | Mean Parti. Diam. of Zirconia (μm) | Relative Density (%) |
|---|---|---|---|---|---|---|---|
| Embod. 7 | 92.5:7.5 | 1500 | 1.41 | 802 | 0.9 | 0.11 | 95 |
| Embod. 8 | 92.5:7.5 | 1450 | 2.02 | 691 | 0.8 | 0.11 | 94 |
| Embod. 9 | 90:10 | 1450 | 0.74 | 1087 | 0.8 | 0.12 | 96 |
| Embod. 10 | 90:10 | 1500 | 0.98 | 860 | 0.9 | 0.12 | 96 |
| Embod. 11 | 90:10 | 1550 | 1.02 | 839 | 1.0 | 0.11 | 98 |
| Embod. 12 | 90:10 | 1450 | 1.50 | 801 | 0.8 | 0.12 | 95 |
| Embod. 13 | 90:10 | 1450 | 1.70 | 842 | 0.8 | 0.12 | 94 |
| Embod. 14 | 90:10 | 1450 | 1.78 | 746 | 0.8 | 0.12 | 94 |
| Embod. 15 | 90:10 | 1450 | 2.07 | 735 | 0.80 | 0.12 | 93 |
| Embod. 16 | 90:10 | 1450 | 2.20 | 603 | 0.8 | 0.12 | 93 |
| Embod. 17 | 90:10 | 1550 | 1.67 | 653 | 1.6 | 0.15 | 96 |
| Compara. Exam. 2 | 90:10 | 1550 | 2.15 | 591 | 1.7 | 0.17 | 94 |
| Embod. 18 | 90:10 | 1600 | 1.62 | 614 | 1.8 | 0.14 | 95 |
| Compara. Exam. 3 | 90:10 | 1600 | 2.11 | 584 | 2.0 | 0.15 | 95 |
| Compara. Exam. 4 | 90:10 | 1450 | 2.23 | 551 | 0.8 | 0.12 | 93 |
| Compara. Exam. 5 | 90:10 | 1450 | 2.36 | 480 | 0.8 | 0.12 | 93 |
| Embod. 19 | 85:15 | 1600 | 0.95 | 1054 | 1.0 | 0.13 | 98 |
| Embod. 20 | 85:15 | 1550 | 1.09 | 870 | 0.9 | 0.13 | 98 |
| Embod. 21 | 85:15 | 1500 | 1.44 | 863 | 0.8 | 0.12 | 97 |
| Embod. 22 | 85:15 | 1500 | 1.72 | 706 | 0.8 | 0.12 | 96 |
| Embod. 23 | 85:15 | 1450 | 2.10 | 684 | 0.8 | 0.12 | 94 |
| Embod. 24 | 85:15 | 1600 | 0.98 | 887 | 1.0 | 0.11 | 97 |
| Embod. 25 | 80:20 | 1600 | 0.85 | 827 | 0.9 | 0.15 | 98 |
| Embod. 26 | 80:20 | 1550 | 1.07 | 903 | 0.8 | 0.14 | 97 |
| Embod. 27 | 80:20 | 1500 | 1.50 | 750 | 0.8 | 0.14 | 95 |
| Embod. 28 | 80:20 | 1450 | 1.96 | 606 | 0.7 | 0.13 | 93 |
| Embod. 29 | 80:20 | 1600 | 0.91 | 872 | 1.0 | 0.11 | 96 |
| Compara. Exam. 6 | 70:30 | 1500 | 1.48 | 581 | 0.7 | 0.17 | 94 |

For the resulting composite ceramic body, the observation of pores, the evaluation of bending strength, the measurement of the mean particle diameter of alumina particles and the measurement on mean particle diameter of nano-zirconia particles and the measurement of the relative density of the composite ceramic body were conducted.

<Observation of Pores>

The pores of the composite ceramic body were observed using SEM (Scanning Electron Microscope). More particularly, first, the test pieces were cut upon which cross sections of the test pieces were ground and thermal etching was conducted to form a grain boundary. Thermal etching was conducted at temperatures lower than a firing temperature by 200° C. for 20 minutes. Then, three rectangular viewing fields were prepared for each test piece and each of the viewing fields had a shape with 45 μm×60 μm in cross section. The three viewing fields were observed with a magnification of ×2000, thereby obtaining a mean value of a surface area percentage of the specified pores in the three viewing fields. This mean value was evaluated to be the pore surface area percentage of each test piece.

In obtaining the pore surface area percentage, the mean particle diameter of the alumina particles was obtained by initially referring to the SEM observation photographs and subsequently conducting treatments (described below) on the SEM observation photographs using image-processing software. Table 1 shows the mean particle diameter of the alumina particles and the pore surface area percentage.

In image processing, the SEM observation photographs were subjected to binary treatment with a given threshold value. In the SEM observation photographs, black color portions indicated the pores with white color portions indicating areas other than the pores. Subsequently, if a white-colored isolated point is present in an inside area of a region exhibiting a pore, then, such an area was determined to be part of a pore.

Next, a white and black color inversion was made between the pores and the other areas, thereby identifying the pores. Thereafter, among the extracted pores, a specified pore, having a cross section equivalent to or greater than a circle having a diameter equal to or greater than a mean particle diameter of the alumina particles, was identified. Then, dividing a total surface area of the specified pores by a surface area of a whole viewing field resulted in a pore surface area percentage of such a viewing field.

Such operations were conducted on one test piece by three viewing fields with a resultant mean value being indicated in Table 1 as the pore surface area percentage.

As will be apparent from Table 1, the test pieces Nos. E1-E29 had the pore surface area percentages each in a value of 2.2% or less.

For reference, further, FIG. 2 shows the SEM observation photograph of the test piece E10. In FIG. 2, a white looking area indicates a nano-zirconia particle 3. A gray looking area indicates an alumina particle 2, a contour of which is surrounded with a line with a reference 2. Black looking areas indicate pores, among which an area, greater than the cross sectional area equivalent to the circle with the diameter equal to or greater than the mean particle diameter of the alumina particles, indicates a specified pore 4.

<Bending Strength>

Figure 1:
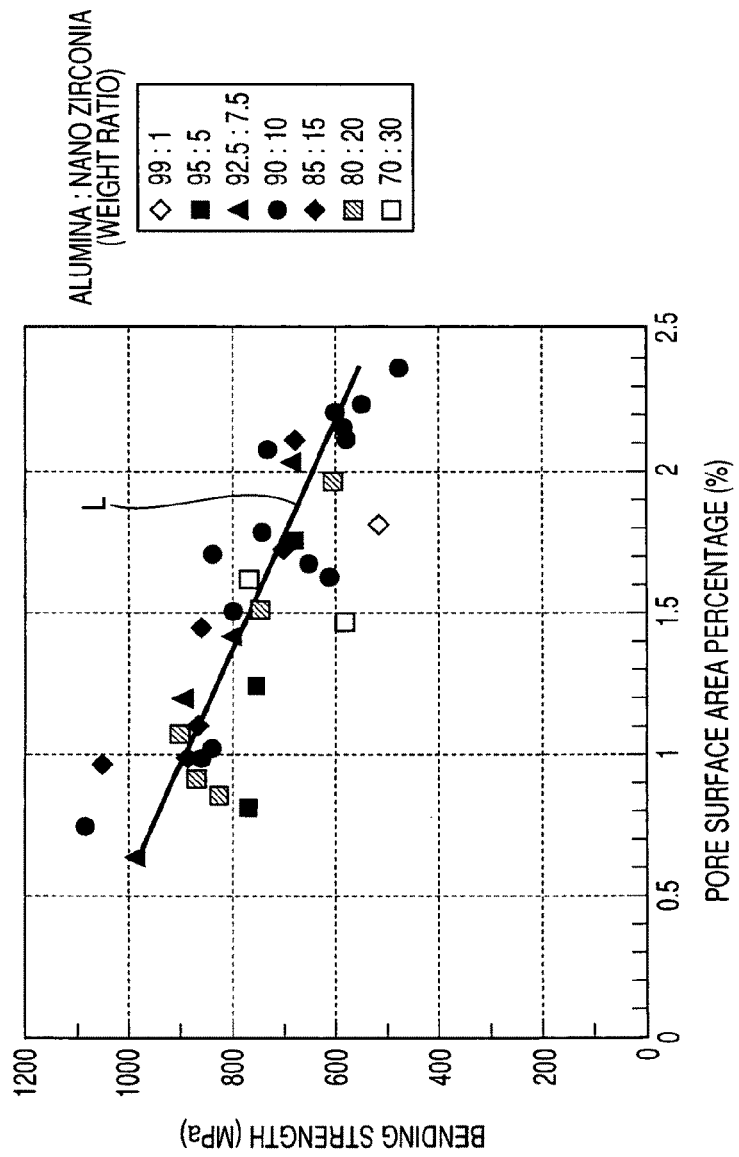
FIG. 1 is an illustrative view showing the relationship between a surface area percentage of pores equal to or greater than a mean particle diameter of alumina in a first embodiment according to the present invention.

For checking bending strength, fired test pieces were processed and evaluations were made on strength using a three-point bending test method in a bending strength test method under JIS R 1601. Results are collectively indicated on Table 1. Further, FIG. 1 represents the relationship between the surface area percentage of the pores equal to or greater than the mean particle diameter of alumina and bending strength. In FIG. 1, bending strength (MPa) is plotted on a longitudinal axis and the pore surface area percentage (%) is plotted on a horizontal axis. In FIG. 1, various plots indicate results of the various test pieces (Test pieces Nos. E1-E29 and Test pieces Nos. C1-C6). In addition, the various plots are distinguished in shape from each other in terms of a weight percentage of alumina to nano-zirconia as shown by a legend in FIG. 1.

From these results, it turns out that the pore surface area percentage and bending strength fall in the relationship indicated by a straight line. Also, a straight line L, shown in FIG. 1, is derived by a least-squares method.

<Average Particle Diameter of Alumina Particles>

The mean particle diameter of alumina particles was obtained by observing the SEM photographs. More particularly, the test pieces were cut with cross sections being ground and, with a view to allowing the grain boundaries to be clear, thermal etching treatments were carried out. Thermal etching treatments were conducted at temperatures lower than the firing temperature by 200° C. for 20 minutes. Carbon was vapor-deposited on each of the test pieces for SEM observation. In SEM observations, grain boundaries of a whole of the alumina particles, present in a secondary electron image of SEM with a magnification of ×10000, were traced using image-processing software in a viewing field of a rectangle shape with 8.7 μm×11.6 μm in cross section of each test piece. An equivalent circle diameter of the traced particles was obtained, based on which a mean value of particle diameters of the alumina particles in an observed viewing field was calculated. Then, the foregoing treatments were conducted on three sheets of the observed viewing fields, thereby obtaining a mean particle diameter of the alumina particles in each observed viewing field.

<Average Particle Diameter of Nano-Zirconia Particles>

The mean particle diameter of nano-zirconia particles was obtained by observing the SEM photographs. More particularly, the test pieces were cut with cross sections being ground and, with a view to allowing the grain boundaries to be clear, thermal etching treatments were carried out. Thermal etching treatments were conducted at temperatures lower than the firing temperature by 200° C. for 20 minutes. Carbon was vapor-deposited on the test pieces for SEM observation. In SEM observations, grain boundaries of a whole of the nano-zirconia particles, present in a secondary electron image of SEM with a magnification of ×10000, were traced using image-processing software in a viewing field of a rectangle shape with 8.7 μm×11.6 μm in cross section of each test piece. An equivalent circle diameter of the traced particles was obtained, based on which a mean value of particle diameters of the nano-zirconia particles in an observed viewing field was calculated. Then, the foregoing treatments were conducted on three sheets of the observed viewing fields, thereby obtaining a mean particle diameter of the nano-zirconia particles in each observed viewing field.

<Relative Density of Composite Ceramic Body>

Relative Density=(Actual Density of Test Piece)/(Theoretical Density of Test Piece)×100

First, respective theoretical densities of the test pieces were calculated in terms of theoretical densities of alumina and zirconia and a weight percentage of alumina and zirconia. Then, weights and dimensions of the resulting test pieces were measured, thereby obtaining actual densities of the various test pieces. Subsequently, the relative densities were obtained in terms of the actual densities relative to the theoretical densities of the various test pieces. In preparing the various test pieces, the weight percentages were preliminarily clarified upon weighing the alumina particles and the nano-zirconia particles.

Although it has been known that alumina generally has bending strength of approximately 600 MPa, the test pieces E1 to E29 of the embodiment 1 had bending stresses of 600 MPa or more while the test pieces C1 to C6 of the Comparative Example had bending stresses less than 600 MPa.

As known from Table 1 and FIG. 1, it turns out that the smaller the pore surface area percentage, the higher will be the bending strength. The pore surface area percentage, lying at a point at which bending stress lies on the straight line L with a value of 600 MPa is 2.2%. Thus, it becomes possible to confirm that strength can be improved when the pore surface area percentage falls in a value of 2.2% or less.

Further, as indicated in an embodiment 3 described below, when using the composite ceramic body as a gas sensing element, the composite ceramic body is required to have bending strength of 600 MPa or more. In this respect, forming the composite ceramic body with the pore surface area percentage falling in the value of 2.2% or less results in a remarkable advantageous effect.

Under a circumstance where bending strength is of 680 MPa or more, further, as will be indicated in the embodiment 3 described below, even if a protective cover having a structure with priority given to response (see FIG. 6) is employed, it becomes possible to preclude the occurrence of element cracks. With such a view in mind, upon introducing the pore surface area percentage, required for bending strength to be of 680 MPa or more, from the results mentioned above, it turns out that the pore surface area percentage is 1.5% or less.

That is, with the pore surface area percentage selected to be 1.5% or less, the composite ceramic body can have further improved bending strength with further improved strength against thermal shock. Thus, even if the protective cover, having the structure with priority given to response, is employed, the occurrence of water-incursion cracks of the gas sensing element can be adequately avoided. That is, it becomes possible to obtain a gas sensing element with excellent response having a capability of precluding the occurrence of water-incursion cracks.

Here, the reason why the improvement in bending strength leads to improvement in strength against thermal shock will be explained below.

In general, the resistance to cracking due to thermal stress of material caused by a temperature distribution occurring on a component member is referred to as a thermal shock fracture resistance coefficient R that will be given by the following equation:

$$R = \delta(1-v)/E\alpha$$

where $\delta$: bending strength, $v$: Poisson's ratio, $E$: Young's modulus and $\alpha$: thermal expansion coefficient. From this equation, it can be understood that improving bending strength enables the improvement in the thermal shock fracture resistance coefficient R with a resultant in increase in strength against thermal shock. Bending strength $\delta$ can be adjusted in a method of manufacturing the component member. Meanwhile, the thermal expansion coefficient $\alpha$ can be adjusted to a slight extent and the Young's modulus E and Poisson's ratio v are determined by the material.

Accordingly, improving bending strength results in the improvement in the thermal shock fracture resistance coefficient R with resultant increase in strength against thermal shock.

As set forth above, the present invention provides a composite ceramic body having increased strength.

(Second Embodiment)

A gas sensing element 5 of a second embodiment according to the present invention is described below with reference to FIGS. 3 and 4. The gas sensing element 5 is comprised of the composite ceramic body implementing the present invention.

With the gas sensing element 5 of the present embodiment is incorporated in a gas sensor installed on an automotive engine at an exhaust system thereof in use. The gas sensor is utilized for performing a combustion control of an engine upon measuring an oxygen concentration of exhaust gases to detect an air/fuel ratio of the engine based on a measured value.

Figure 3:
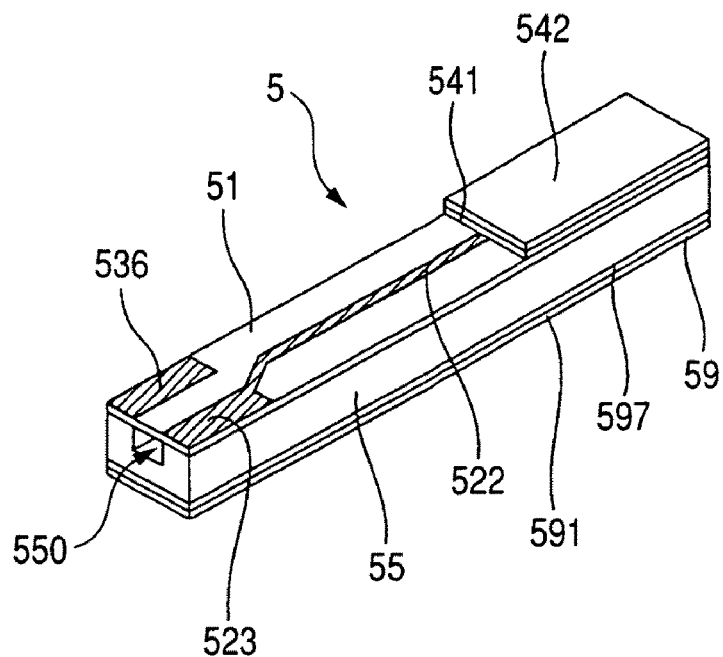
FIG. 3 is an illustrative view showing a gas sensing element of a second embodiment according to the present invention.
Figure 4:
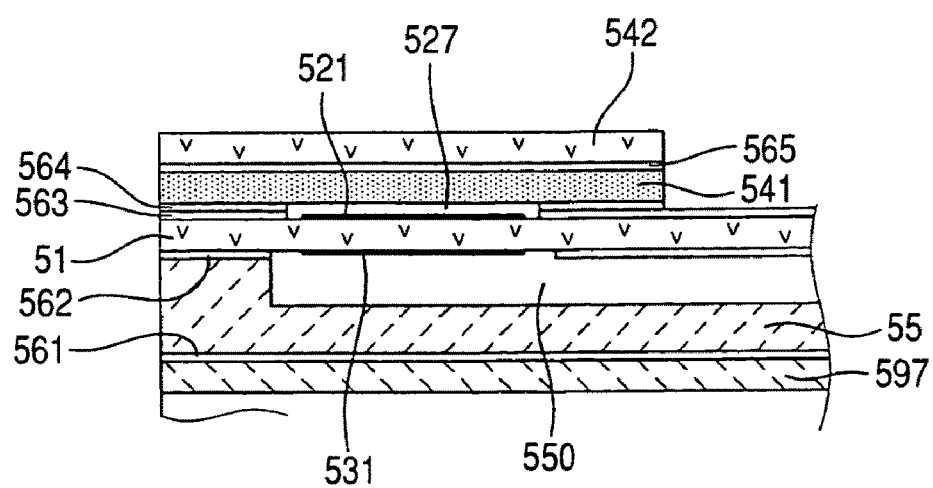
FIG. 4 is a cross-sectional view showing the gas sensing element of the second embodiment.

As shown in FIGS. 3 and 4, the gas sensing element 5 of the present embodiment takes the form of a structure including a reference gas chamber forming plate 55, a solid electrolyte plate 51, a diffusion layer 541 and a shielding layer 542.

The reference gas chamber forming plate 55 has a U-shape in cross section and includes recessed portion 550 acting as a reference gas chamber to which reference gas is introduced from outside.

The solid electrolyte plate 51 includes a measuring gas electrode 521 and a reference electrode 531.

Further, the diffusion layer 541 is stacked onto the solid electrolyte plate 51 so as to cover the measuring gas electrode 521 and the shielding layer 542 is stacked so as to cover the shielding layer 542.

Furthermore, the gas sensing element 5 of the present embodiment has a ceramic heater 59 unitarily provided on the reference gas chamber forming plate 55 at one surface thereof in opposition to the other surface facing the solid electrolyte plate 51.

The ceramic heater 59 is comprised of a heater sheet 591, a heating element formed on the heater sheet 591, and a heater insulating plate 597 stacked in place so as to cover the heating element.

Intervening between the heater insulating plate 597 and the reference gas chamber forming plate 55, between the reference gas chamber forming plate 55 and the solid electrolyte plate 51, and between the diffusion layer 541 and the shielding layer 542 are adhesive layers 561, 562 and 565. In addition, an insulating layer 563 and the adhesive layer 564 are disposed between the solid electrolyte plate 51 and the diffusion layer 541.

The solid electrolyte plate 51 is made of partially stabilized zirconia in which 6 mol % of yttria is added to zirconia.

Further, the reference gas chamber forming plate 55, the diffusion layer 541, the heater sheet 591, the heater insulating plate 595 and 597, the insulating layer 563, the adhesive layers 561, 562, 564 and 566, and the shielding layer 542 constitute the composite ceramic body of the present invention.

Accordingly, with these layers, nano-zirconia particles are dispersed in a matrix of the alumina particles. Among the pores appearing on the cross section, pore surface area percentage, representing the percentage of the total surface area of the specified pores having the cross sectional area equal to the circle with the diameter greater than the mean particle diameter of the alumina particles lies in the value of 2.2% or less.

The solid electrolyte plate 51 has one side formed with the reference electrode 531 placed in face-to-face relation to the recessed portion 550 in the form of the reference gas camber and the other side on which the measuring gas electrode 521 is formed.

The insulating layer 563 and the adhesive layer 564 have areas, facing the measuring gas electrode 521, which are formed with windows.

As shown in FIG. 4, moreover, with the insulating layer 563 and the adhesive layer 564 stacked on each other, the windows, formed in the insulating layer 563 and the adhesive layer 564, respectively, provide a small chamber 527 in which the measuring gas electrode 521 is accommodated.

Further, measuring gas is admitted to the small chamber 527 via the diffusion layer 541.

Next, a method of manufacturing the gas sensing element 5 of the present embodiment is simply described below.

A green sheet for the solid electrolyte plate 51 is prepared by a doctor blade method or an extrusion molding method. Subsequently, the green sheet is provided with printed portions for the measuring gas electrode 521 and the reference electrode 531, respectively.

An unfired compact body for the reference gas chamber forming plate 55 is prepared by injection molding, cutting and forming, press forming and glue forming, etc.

Further, green sheets for the reference gas chamber forming plate 55, the shielding layer 542 and the diffusion layer 541, etc., are prepared by a doctor blade method or an extrusion molding method.

Furthermore, a greet sheet for the heater sheet 591 is provided with a printed portion for the heating element, etc.

In forming the adhesive layers 561, 562, 564 and 566 and the insulating layer 563, pastes for the adhesive layers and the insulating layer are prepared and then printed on the relevant greet sheets. Those, in which the windows are provided, are formed by screen printing with the use of pastes. Likewise, the heater insulating plate 597 is formed by screen printing with the use of paste.

As set forth above, the prepared green sheets are stacked on one another in an order shown in FIG. 3 and then stacked. This allows these green sheets to be stick to each other due to adhesiveness (i.e. natural stickness) of the adhesive layers 561, 562, 564 and 565, thereby forming an unfired compact body. The unfired compact body is subjected to degreasing treatment at a temperature of 500° C. for 25 hours, after which the unfired compact body is heated up to a temperature of 1500° C. for firing to obtain a fired compact body.

Thereafter, the fired compact body is cooled from 1500° C. to room temperature, thereby obtaining the gas sensing element 5 of the present embodiment.

Under a situation where the composite ceramic body of the present invention forms a part of the gas sensing element for detecting a specified gas concentration in measuring gas, the composite ceramic body can withstand thermal shock with a resultant capability of preventing the occurrence of water-incursion cracks set forth above.

(Third Embodiment)

Figure 5:
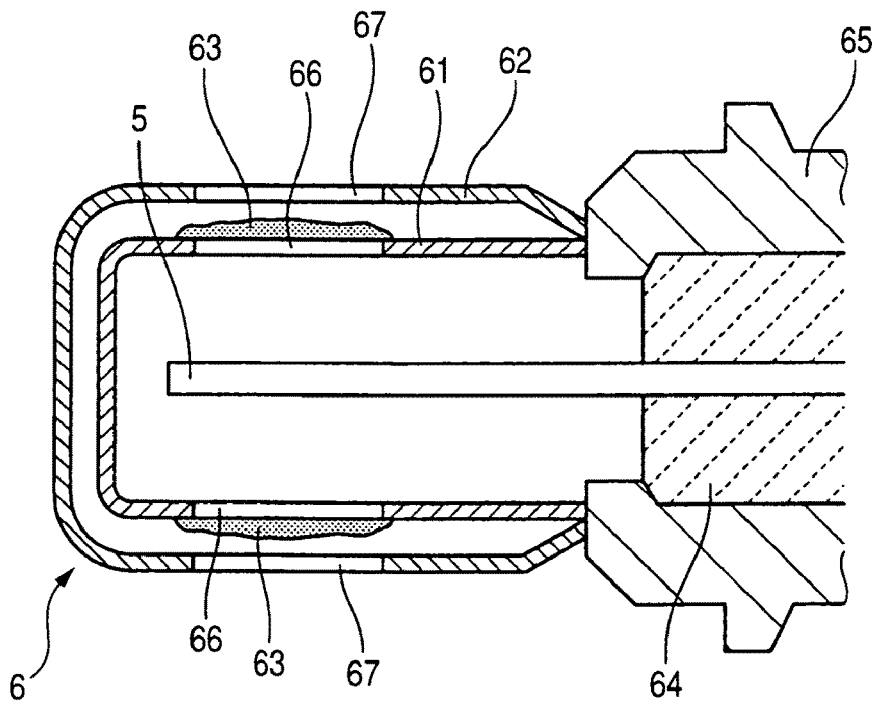
FIG. 5 is a cross-sectional view showing a gas sensor having a protective cover provided with protecting means in a third embodiment according to the present invention.
Figure 6:
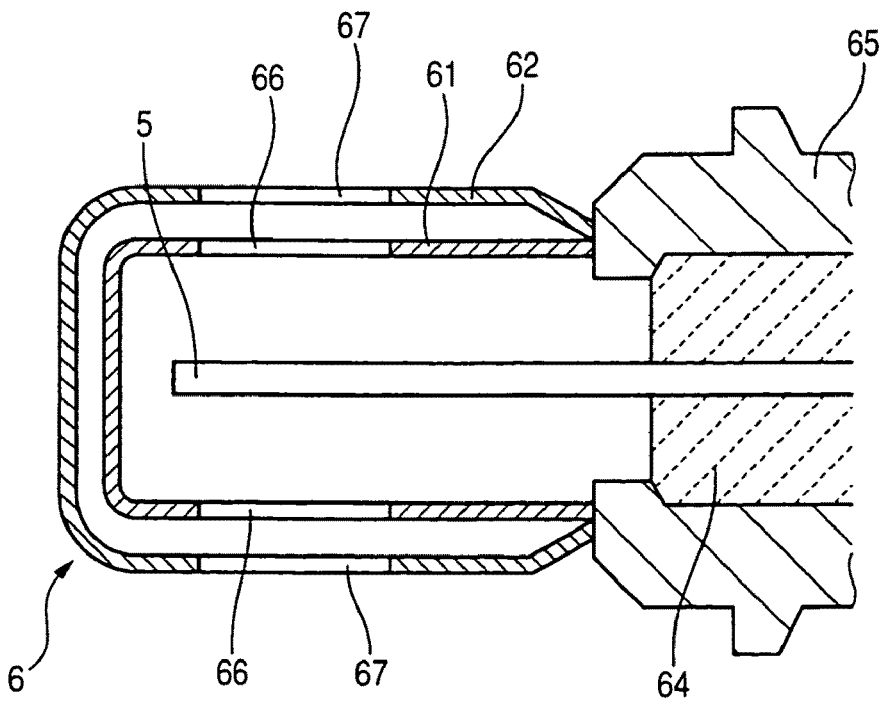
FIG. 6 is a cross-sectional view showing the gas sensor of the third embodiment having the protective cover in which no protecting means is provided.

As shown in FIGS. 5 and 6, a third embodiment is an example in which with a gas sensor 6, having protective covers 61 and 62 disposed so as to cover the gas sensing element 5 shown with reference to FIG. 2, an inherent stress of the gas sensing element 5, occurring when subjected to water incursion, is measured on a simulation with a water-incursion cracks analysis software.

That is, simulations were conducted under two kinds of conditions directed to one case (see FIG. 5) wherein those, having shapes as shown in FIG. 3 of Japanese Utility Model Application Publication 4-11461, were adopted as the protective covers 61 and 62 under which protecting means (a protective layer 63) was provided (see FIG. 5) and the other case (see FIG. 6) wherein no protecting means was provided.

The simulations were conducted by analyzing stress occurring on the gas sensing element 5 when with the gas sensor 6 installed on an exhaust pipe of a motor vehicle in actual practice, assumed water incursion (water-droplet adhesion) during a startup of an engine, occurred on the gas sensing element 5. Moreover, the gas sensing element 5 during the water incursion had a temperature set to an actual temperature of 750° C.

Further, the structure of the stack type shown in the second embodiment was adopted as the gas sensing element 5 to be different in structure from the cup type disclosed in FIG. 3 of Japanese Utility Model Application Publication 4-11461.

Furthermore, providing the protective layer 64 as shown in FIG. 5 enables the suppression of water incursion of the gas sensing element 5. However, there is a likelihood that it takes a longer time for measuring gases (exhaust gases) to reach a detecting section of the gas sensing element 5 with a resultant disadvantage in view of responsiveness. On the contrary, under a case where no protective layer 64 is provided as shown in FIG. 6, no such situation occurs with resultant excellent responsiveness.

As shown in FIGS. 5 and 6, more particularly, the gas sensor 6, used for simulation, takes the form of a structure in which bottomed cylindrical double-layered protective covers 61 and 62 located so as to cover the gas ensign element 5 retained with a housing 65 by means of a porcelain insulator 64. The protective covers 61 and 62 have sidewalls formed with opening portions 66 and 67. In addition, porous protective layers 63 are provided so as to cover the opening portions 66 of the inside protective cover 61.

The protective covers 63 are adhered onto the protective cover 61 by plasma spraying powder of materials composed of magnesia and spinel.

The opening portions 66 and 67 have opening diameters of 0.8 mm and the protective layer 63 has a thickness of 500 μm.

Moreover, the opening portion 66 of the inside protective cover 61 and the opening portion 67 of the outside protective cover 62 are formed in positions overlapping each other. Besides, the gas sensor 6 takes the form of the structure shown in Japanese Utility Model Application Publication 4-11461.

As results of the simulations, in a case (see FIG. 5) where the protecting means (protective layer 63) is provided, the resulting stress falls in a value of 600 MPa. In contrast, in another case where no protecting means (protective layer 63) is provided, the resulting stress falls in a value of 680 MPa. As will be apparent from the result of the present embodiment and the test result of the first embodiment mentioned above, in the case where no protecting means is provided, it is considered that the pore surface area percentage of the composite ceramic body, forming the gas sensing element 5, needs to be suppressed to a value of 1.5% or less whereas in the other case where the protecting means is provided, the pore surface area percentage is able to have a value of 2.2% or less.

What is claimed is:

1. A composite ceramic body consisting essentially of:
   a matrix of alumina particles having a mean particle diameter ranging from 0.7 to 1.8 μm; and
   nano-zirconia particles having particle diameters of 0.15 μm or less;
   wherein the alumina particles and the nano-zirconia particles fall in a weight percentage ratio ranging from 80:20 to 95:5 respectively with a relative density of 93% or more; and
   wherein in a cross section of the composite ceramic body, a total sum of surface areas of pores, having cross-sectional areas equal to or greater than surface areas of circles having the same diameters as a mean particle diameter of the alumina particles, falls in a value of 2.2% or less with respect to a whole of the cross-sectional area.

2. The composite ceramic body according to claim 1, wherein the composite ceramic body forms a part of a gas sensing element for detecting a specified gas concentration.

3. The composite ceramic body according to claim 1, wherein the composite ceramic body is made of the alumina particles and the nano-zirconia particles having the weight percentage ratio ranging from 85:15 to 92.5:7.5.

4. The composite ceramic body according to claim 1, wherein in the cross section, the total sum of the surface areas of the pores, having the cross-sectional areas equal to or greater than the surface areas of the circles with the same diameters as the mean particle diameter of the alumina particles falls in a value of 1.5% or less with respect to the whole of the cross-sectional areas.

5. The composite ceramic body according to claim 2, wherein the composite ceramic body is made of the alumina particles and the nano-zirconia particles having the weight percentage ratio ranging from 85:15 to 92.5:7.5.

6. The composite ceramic body according to claim 2, wherein in the cross section, the total sum of the surface areas of the pores, having the cross-sectional areas equal to or greater than the surface areas of the circles with the same diameters as the mean particle diameter of the alumina particles falls in a value of 1.5% or less with respect to the whole of the cross-sectional areas.

7. The composite ceramic body according to claim 3, wherein in the cross-section, the total sum of the surface areas of the pores, having the cross-sectional areas equal to or greater than the surface areas of the circles with the same diameters as the mean particle diameter of the alumina particles falls in a value of 1.5% or less with respect to the whole of the cross-sectional areas.

8. The composite ceramic body according to claim 1, wherein the pore surface area percentage is 0.63% or more.

* * * * *